United States Patent [19]

Shue

[11] Patent Number: 4,723,555

[45] Date of Patent: Feb. 9, 1988

[54] MULTI-FUNCTIONAL RADIO/WIRE STETHOSCOPIC APPARATUS

[75] Inventor: Ming-Jeng Shue, Taichung, Taiwan

[73] Assignee: L'Air Liquide, Paris, France

[21] Appl. No.: 926,578

[22] Filed: Nov. 4, 1986

[30] Foreign Application Priority Data

Sep. 24, 1986 [TW] Taiwan ............................. 75209023

[51] Int. Cl.⁴ ............................................. A61B 5/02
[52] U.S. Cl. ................................... 128/715; 128/680; 128/773
[58] Field of Search .................. 128/680, 773, 715

[56] References Cited

U.S. PATENT DOCUMENTS

| 4,248,241 | 2/1981 | Tacchi | 128/715 |
|---|---|---|---|
| 4,438,772 | 3/1984 | Slavin | 128/715 |
| 4,458,693 | 7/1984 | Badzinski et al. | 128/715 |
| 4,619,268 | 10/1986 | Uphold et al. | 128/715 |

Primary Examiner—William E. Kamm
Assistant Examiner—Timothy Keegan
Attorney, Agent, or Firm—Lee C. Robinson, Jr.

[57] ABSTRACT

A multi-functional radio/wire stethoscopic apparatus includes: a housing unit having a plurality of control switches and sockets provided therein for hand operation; a radio wave transmitting device and a wire transmission line disposed in the housing unit for signal transmitting operations; an audio-wave guiding device positioned on top of the housing unit for receiving sound waves; a plurality of microphones disposed in the audio-wave guiding device and electrically connected to the radio wave transmitting device and the wire transmission line; an upper casing detachably connected to the housing unit; and a chest piece with sound detecting arrangement functionally connected to an upper end of the upper casing; thereby, during auscultation and bedside teaching, sound waves from a patient's body will be converted into electrical signals and transmitted for facilitating correct diagnosis through a radio/recorder set and an interface of audio wave control device electrically connected to the housing unit.

5 Claims, 7 Drawing Figures

MULTI-FUNCTIONAL RADIO/WIRE STETHOSCOPIC APPARATUS

BACKGROUND OF THE INVENTION

This invention relates to a stethoscopic apparatus, and more particularly to a type of radio/wire stethoscopic apparatus designed for multiple auscultation and historical recording of a patient.

A stethoscope is an indispensable medical instrument for diagnosing the illness of patients by doctors. However, problems suffered by the conventional stethoscopes are as follows:

(1) The structure of conventional stethoscopes usually comprises a chest piece provided at one end of a rubber tube, and a pair of eartips arranged at another end of the rubber tube through a pair of flexible binaurals. By positioning the chest piece on the patient's body, diagnosis is made from the sound detected by the chest piece through either a diaphragm or a bell thereof. The sound generated from the patient's body is usually very weak and also varies. Correct diagnosis cannot be made easily because transformation of the detected sound is often caused by the binaurals of the conventional stethoscopes.

(2) In order to allow the user to listen to the patient's body without interference by external noise, the binaurals of the conventional stethoscope must be resilient, which is uncomfortable for the user.

(3) Conventional stethoscopes are usually designed for a single user. If consultation is required for the same patient or bed-side teaching has to be conducted as in academically affiliated hospitals, each observer needs to perform the auscultation one after another on the same patient. At the same time, different types of stethoscopes used at different times may result in different detected sounds. Therefore, not only is it inconvenient for the patient, particularly a female one, but also it is difficult for each observer to observe the same sound for correct diagnosis.

(4) As conventional stethoscopes are designed to perform auscultation only on the spot, it is difficult to diagnose from a very weak and transient sound from the suspected body portion of a patient, and, moreover, there is no recording function provided for conventional stethoscopes to record the required sound for the patient's history for correct diagnosis as well as for teaching purposes.

SUMMARY OF THE INVENTION

It is accordingly a primary object of this invention to provide a multi-functional radio-wire stethoscopic apparatus which can precisely detect the noise of the internal organs and clearly amplify it so as to exactly present the detected sound for enabling diagnosis.

It is another object of this invention to provide a multi-functional radio/wire stethoscopic apparatus with which earphones can be used for facilitating diagnostic operations and also for the comfort of the user.

It is a further object of this invention to provide a multi-functional radio/wire stethoscopic apparatus by which several users can simultanuously perform auscultation for facilitating consultative diagnosis or teaching purposes.

It is a still further object of this invention to provide a multi-functional radio/wire stethoscopic apparatus through which radio/wire receiving, recording and playing of either the sound detected from the patient's viscera or the discussions held during consultation can be conveniently recorded for later reference.

These and other objects of this invention are achieved by providing a multi-functional radio/wire stethoscopic apparatus, which comprises: a housing unit having a plurality of finger recesses for hand gripping; a radio wave transmitting device and a wire transmission line disposed in the housing unit; a Y-shaped audio-wave guide having a plurality of microphones installed therein fixed at one end on top of the housing unit with the microphones electrically connected to the radio wave transmitting device and wire transmission line; a power switch provided in the housing unit in conjunction with the radio wave transmitting device; a plurality of wire remote control switches and sockets respectively installed in the housing unit for being electrically connected to a radio/recorder set; and a chest piece having a diaphragm on one side and a bell on another connected to an upper end of the audio-wave guide; thereby, when the chest piece of the multi-functional radio/wire stethoscopic apparatus according to this invention is placed against a body portion of a patient, sound from within the body portion of the patient will be converted into electrical signal by the microphones disposed in the audio-wave guide and transferred to the radio wave transmitting device and the transmission line so that the transmitted sound from the patient's body portion can be either received by individual and/or multiple earphones connected to the stethoscopic apparatus for obtaining correct diagnosis as in consultation and bed-side teaching, or picked up and recorded by the radio/recorder sets electrically connected thereto for historical reference.

Other characteristics and advantages of this invention will become apparent from the following detailed description of a preferred embodiment with reference to the accompanying drawings.

DETAILED DESCRIPTION OF THE PREFERRED EMBODIMENT

Figure 1:
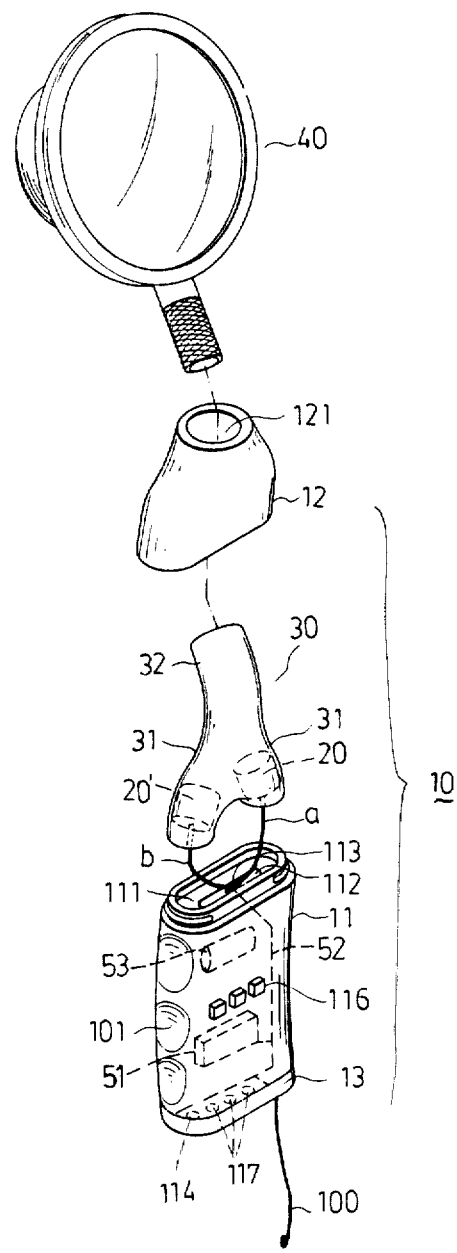
FIG. 1 is an exploded and perspective view of a preferred embodiment of a multi-functional radio/wire stethoscopic apparatus according to this invention.

Referring to FIGS. 1, 2, 3A and 3B, the preferred embodiment of a multi-functional radio/wire stethoscopic apparatus according to this invention comprises in combination: a housing unit 10 which includes a main body portion 11, an audio-wave guide 30, a bottom cover 13 and an upper casing 12; a chest piece 40 and a radio transmitting line 100.

The main body portion 11 is formed in an elongated planular shape with a slight curvature. The portion 11 includes: a plurality of finger recesses 101 provided on one side thereof for comfortable hand gripping; a level surface 111 with a central recess 112 formed by the upper inner edge of the main body portion 11; a recess hole 113 provided in the recess 112; a radio wave transmitting device 51 of conventional construction; and a wire transmission line 52, together with a power source 53 electrically disposed within the body portion 11; a power switch 115 provided in the main body portion 11 and electrically connected between the power source and the radio wave transmitting device and the wire transmission line provided in body portion 11; and a plurality of wire remote control switches 116 installed in the body portion 11. The bottom cover 13 coupled with the main body portion 11 includes a single socket 114 electrically connected to the wire transmission line, which, in turn, is connected to the microphones 20, 20' located in the audio-wave guide 30 through a pair of conductive cords a and b, and a multiple socket 117 electrically connected to the remote control switches 116 of the main body portion 11, and a radio transmitting line 100 electrically coupled with the radio wave transmitting device for transmitting radio waves therefrom.

The Y-shaped audio wave guide 30 is made of flexible material and includes a lower forked portion 31 and an upper branch portion 32. It is positioned in the recess 112 of the body portion 11. The pair of highly sensitive microphones 20, 20' are respectively disposed in the forked portion 31 with the conductive cords a and b of the microphones 20, 20' separately connected to the radio wave transmitting device and the wire transmission line through the recess hole 113. The upper casing 12 is formed in a shape conforming to that of the audio-wave guide 30, but without a forked portion, with an opening 121 formed in a top portion thereof. It is connected to the main body portion 11 with the audio wave guide 30 being completely surrounded thereby and being pressed against the level surface 111 of the body portion 11 for proper positioning, and with a certain length of the branch portion 32 extending out of the opening 121 of the upper casing 12. It shall be appreciated that the connection between the main body portion 11 and the upper casing 12 as well the bottom cover 13 can be made through a kind of halved joint by which the protrusions provided at both ends of the main body portion 11 can be closely engaged with the notches formed in an inner wall of the upper casing 12 and the bottom cover 13 so that assembly and disassembly of the housing unit 10 can be easily and quickly made. Also, batteries required for the power source can be easily placed and replaced in the main body portion 11 through the bottom cover 13, which is detachably connected to the lower end of the main body portion 11.

Figure 3A:
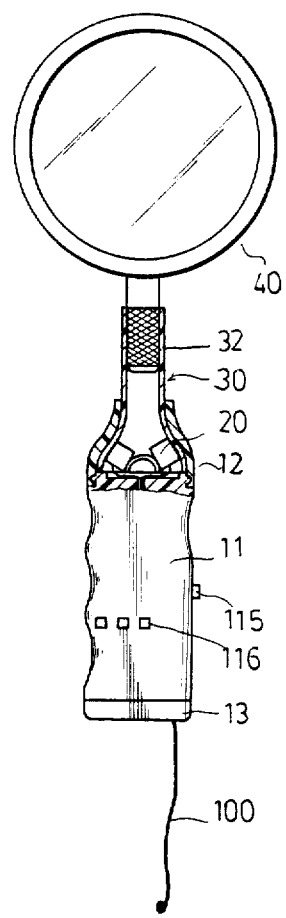
FIG. 3(A) is a partial sectional front view of the assembled preferred embodiment of FIG. 2.

The chest piece 40, of which the structure is almost the same as that of the known stethoscope, has a diaphragm on one side and a bell on the other designed for gathering visceral sounds. The chest piece 40 is sleevingly connected to the upper branch portion 32 as shown in FIG. 3(A).

Figure 2:
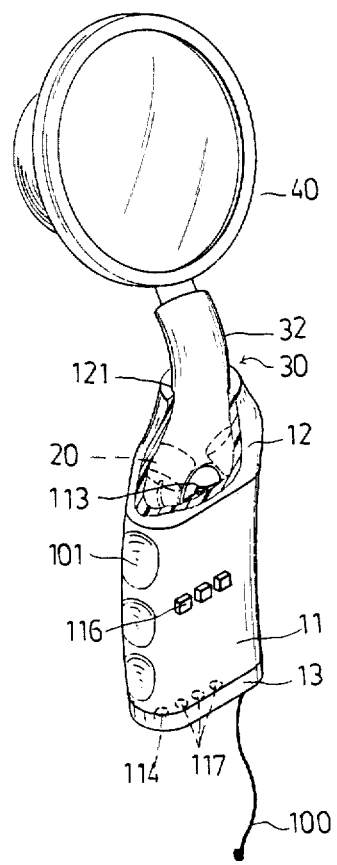
FIG. 2 is a perspective view showing the assembly, partly cut-off, of the preferred embodiment of FIG. 1.
Figure 3B:
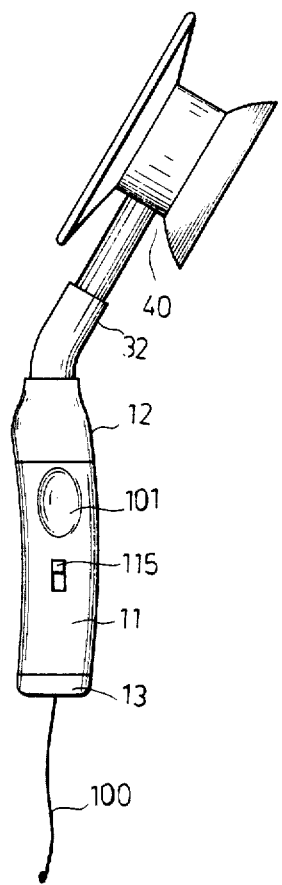
FIG. 3(B) is a side view of the assembled preferred embodiment of FIG. 2.
Figure 4:
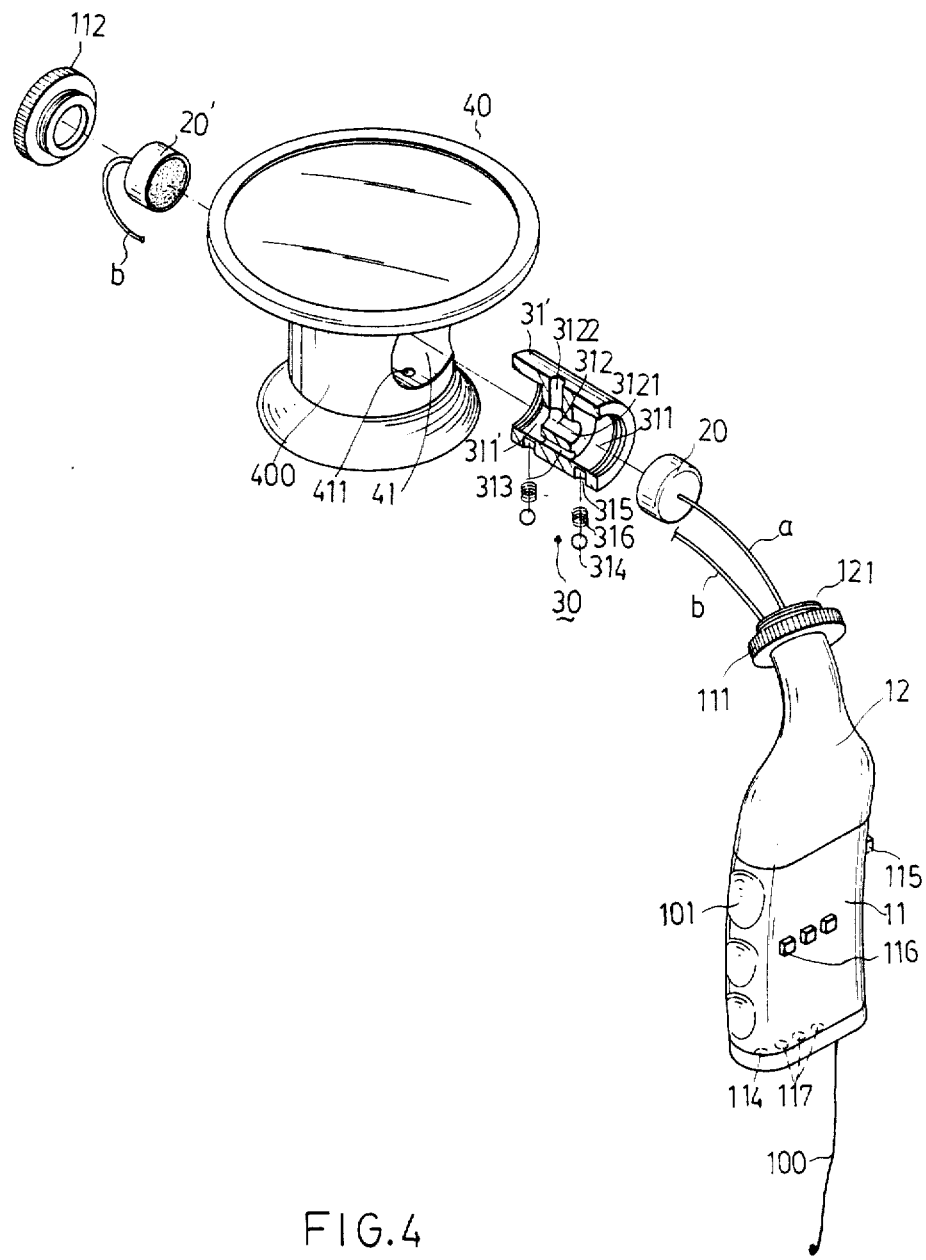
FIG. 4 is an exploded and perspective view of an alternative example of the preferred embodiment of FIG. 1.

Referring to FIG. 4, there is shown an alternative example of the preferred embodiment of a multi-functional radio-wire stethoscopic apparatus according to this invention wherein all members and elements identical with or corresponding to those illustrated in FIGS. 1, 2 and 3(A,B) are indicated by the same reference numerals, and in which, therefore, explanation of those members or elements is omitted hereinbelow.

Figure 5:
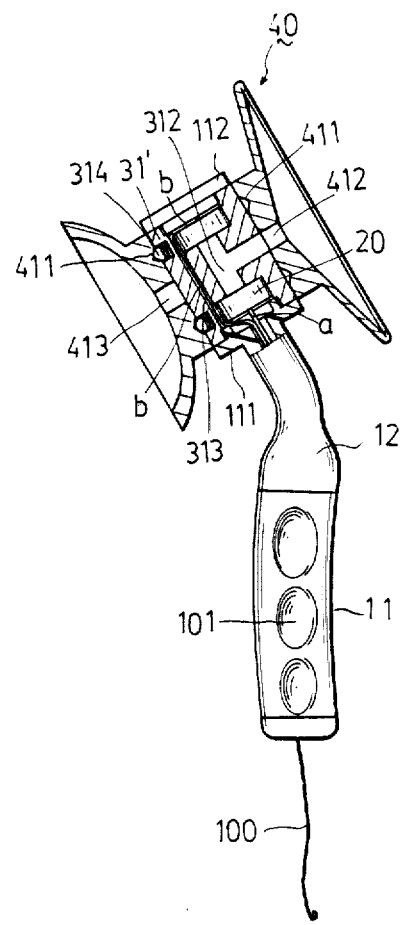
FIG. 5 is a partial sectional side view of the preferred embodiment shown in FIG. 4.

In the alternative example, as shown in FIGS. 4 and 5, the audio-wave guide 30' is formed as a hollow cylindrical body 31', including an upper accommodating chamber 311 and a lower accommodating chamber 311' formed at each end for respectively receiving the microphones 20, 20' therein, a three-way opening 312 with a horizontal portion 3121 and a vertical portion 3122 provided in a central portion thereof in communication with the upper and lower accommodating chambers 311 and 311', a penetrating groove 313 formed beside the horizontal portion 3121 of the three-way opening 312 for receiving the conductive cord b of the microphone 20', and a plurality of steel balls 314, each of which is matched with a spring, separately disposed in a plurality of openings 315 formed in an external wall of the cylindrical body 31'. The chest piece 40 has a through opening 41 horizontally located in a stem portion 400 in conjunction with the periphery of the cylindrical body 31' of the audio-wave guide 30' with a plurality of orifices 411 formed in an inner wall of the through opening 41 in communication with the openings 315 where the steel balls 314 are disposed, and a pair of communication openings 412 and 413 respectively formed in both ends of the stem portion 400, as shown in FIG. 5.

As shown in FIGS. 4 and 5, the audio-wave guide 30' includes a lower cover 111, which is connected to a slightly curved upper portion of the upper casing 12, and an upper cover 112. During assembly, the cylindrical body 31' is properly positioned in the through opening 41 of the chest piece 40 with the vertical portion 3122 of the three-way opening 312 aligned with the opposing communication openings 412 or 413, and the steel balls 314 respectively located in the orifices 411 so as to keep the cylindrical body 31' in position in the through opening 41 of the chest piece 40. The conductive cords a and b of the microphones 20, 20', which are separately located in the lower and upper chambers 311, 311', are respectively connected to the radio wave transmitting device and the wire transmission line through the upper opening 121 of the upper casing 12 with the cord b passing through the penetrating hole 313 of the cylindrical body 31'. The lower cover 111, together with the upper casing 12, and the upper cover 112 are respectively screw-connected to both ends of the audio-wave guide 30', and the assembly is completed accordingly.

Figure 6:
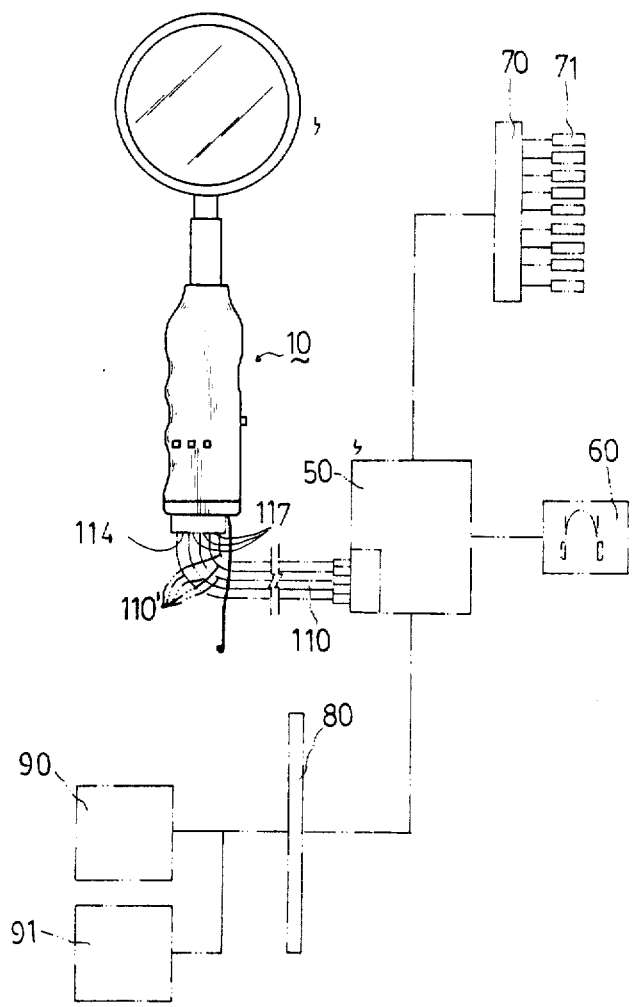
FIG. 6 is a schematic operational illustration of the preferred embodiments respectively shown in FIGS. 1 and 4.

Referring to FIGS. 1, 4 and 6, when the preferred embodiment is used for consultation or for bed-side teaching, an electrical connection cord 110 is connected between the socket 114 of the preferred embodiment of this invention and a socket adaptor of a known radio/-recorder set 50 from which a single headphone 60 or a multiple earphone adaptor 70 with numerous earphones connected thereto can be conveniently coupled with the radio/recorder set 50. Therefore, when the chest piece 40 is placed on the patient's body portion, sound from the body portion will be picked up by the microphones 20, 20' and converted into electrical waves which are transferred to the radio wave transmitting device as well as to the wire transmission lines and transmitted therefrom either as a radio signal, which is transmitted from the transmitting line 100 and received by the radio/recorder set 50 for being transduced into radio sound through the speaker of the radio/recorder set 50, or as a wire signal relayed to the radio/recorder 50 through the connection cord 110 for being clearly received by the headphone 60 or the earphones 71 simultaneously. Any comments made by the examining head doctor, who uses the radio/wire stethoscoping device during bed-side teaching, will be picked up by the microphones 20 through either the diaphragm or the bell of the chest piece 40 and relayed through both the radio wave transmitting device and the wire transmission line in the main body portion 11 to all the listeners who either wear the earphones 71 or use the radio/recorder sets to perform the auscultation at the same time. In addition, if audio file is required, the audio signals from the patient's body portion can be conveniently recorded in the radio/recorder set 50 for later examination. On the other hand, if further information is required for data processing and historical filing from the patient, an interface of audio control device 80 can be electrically connected to the output of the radio/recorder set 50, and an oscillograph 90 and a plotting instrument 91 may be functionally coupled with the output of the interface of audio control device so that audio signals from the patient's body portion can be converted into visual display information.

It shall be appreciated that the preferred embodiment of this invention simultaneously operates by both radio and wire. If no radio operation is required, by turning off the power switch 115, as shown in FIG. 3(B), and, by electrically connecting the mic-input socket of the radio/recorder set 50 to the socket 114 through a connecting line 110, the same functions without radio operations will be performed by the preferred embodiment as described above.

As shown in FIGS. 1, 4 and 6, a multiple electrical connection cord 110 in the form of a plurality of lines 110' can also be connected between the sockets 117, 114 and the radio/recorder set 50. In this condition, the wire remote control switches 116 provided on the housing unit 10 can be conveniently operated to control the ON and OFF signal receiving, playing, recording, etc., of the radio/recorder set 50 from the housing unit 10 for the sounds picked up by the microphones 20, 20' through the chest piece 40.

Having thus described the invention, it is to be understood that many embodiments thereof will suggest themselves without departing from the spirit and scope of this invention. Therefore, it is intended that the specification and drawings be interpreted as illustrative rather than in a limiting sense.

What is claimed is:

1. A multi-functional radio/wire stethoscopic apparatus having a chest piece for detecting the sound of a patient's body, the apparatus comprising:
   a housing means;
   a radio wave transmitting means electrically installed in said housing means for transmitting radio signals;
   a wire transmission means electrically disposed in said housing means for transmitting wire signals;
   a power supply means provided in said housing means for supplying electrical power to said radio wave transmitting means and wire transmission means;
   an audio-wave guiding means made of flexible material and formed in a Y-shape connected to the housing means for receiving sound from the chest piece; and
   a plurality of microphones electrically connected to said radio wave transmitting means and said wire transmission means for converting the sound picked up from the chest piece into electrical signals.

2. A multi-functional radio/wire stethoscopic apparatus as claimed in claim 1 wherein said housing means comprises:
   a main body portion formed in an elongated planular shape with a plurality of finger recesses provided on a surface thereof;
   a flat surface having a central recess and a recess opening formed therein;
   a power switch on said main body portion for turning ON and OFF said radio wave transmitting means;
   a plurality of wire remote control switches provided on said main body portion;
   a radio/recorder set connected to said remote control switches for receiving, recording, and replaying said radio signals and said wire signals; and
   a plurality of electrical sockets provided in said main body portion and electrically connected to said wire remote control switches and to the radio/recorder set.

3. A multi-functional radio-wire stethoscopic apparatus according to claim 1 wherein said audio wave guiding means comprises a Y-shaped body made of flexible material with a forked portion at one end thereof for receiving the installation of said microphones therein, and an open branch portion at another end coupled with the chest piece.

4. A multi-functional radio/wire stethoscopic apparatus comprising:
   a chest piece including a stem portion having a through opening formed in the stem portion, and a plurality of orifices communicating with said through opening;
   an audio-wave guiding means installed in said through opening of the chest piece for receiving audio waves therein;
   a pair of microphones separately disposed in said audio wave guiding means for converting audio waves picked up in said audio wave guiding means into electrical signals;
   a housing means operatively connected to said audio wave guiding means;
   a radio wave transmitting device installed in said housing means for receiving electrical signals from said microphones and transmitting radio signals corresponding to the received electrical signals;
   a wire transmission means disposed in said housing means for receiving electrical signals from said microphones and transmitting wire signals corresponding to the received electrical signals; and
   a power supply means provided in said housing means in conjunction with said radio wave transmitting device and said wire transmission means for supplying electrical power to said radio wave transmitting device and said wire transmission means.

5. A multi-functional radio/wire stethoscopic apparatus as claimed in claim 4 wherein said audio wave guiding means comprises:
   a cylindrical body having a first accommodating chamber and a second accommodating chamber formed respectively at opposite ends of said cylindrical body for respectively receiving said microphones therein, and a plurality of openings located in an external wall of said cylindrical body;
   a plurality of steel balls disposed in said openings in the external wall of said cylindrical body;

a first cover connected to one of the ends of said cylindrical body of said audio wave guiding means;

each of said microphones having a conductive cord connected to said radio wave transmitting device and said wire transmission means in said housing means; and a second cover connected to the other end of said cylindrical body; whereby, when the chest piece is placed on a patient's body portion, sound waves of the body portion can be picked up by the microphones in said cylindrical body and converted into electrical signals for radio and wire transmission.

* * * * *

UNITED STATES PATENT AND TRADEMARK OFFICE
CERTIFICATE OF CORRECTION

PATENT NO. : 4,723,555
DATED : February 9, 1988
INVENTOR(S) : Ming-Jeng Shue

It is certified that error appears in the above-identified patent and that said Letters Patent is hereby corrected as shown below:

On the title page

The reference to "L'Air Liquide, Paris, France" as assignee to the patent should be deleted.

Signed and Sealed this

Fifth Day of July, 1988

Attest:

DONALD J. QUIGG

Attesting Officer

Commissioner of Patents and Trademarks